(12) United States Patent
Kameshima et al.

(10) Patent No.: US 7,573,037 B1
(45) Date of Patent: Aug. 11, 2009

(54) RADIATION IMAGE PICKUP APPARATUS, ITS CONTROL METHOD, AND RADIATION IMAGE PICKUP SYSTEM

(75) Inventors: Toshio Kameshima, Kumagaya (JP); Chiori Mochizuki, Sagamihara (JP); Tadao Endo, Honjo (JP); Tomoyuki Yagi, Honjo (JP); Katsuro Takenaka, Kodama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/500,323

(22) Filed: Aug. 8, 2006

(30) Foreign Application Priority Data

Aug. 16, 2005 (JP) ............................. 2005-236038

(51) Int. Cl.
*G01T 1/00* (2006.01)
(52) U.S. Cl. ............................................. 250/370.09
(58) Field of Classification Search .................. None
See application file for complete search history.

(56) References Cited

U.S. PATENT DOCUMENTS

| | | | | |
|---|---|---|---|---|
| 4,689,487 | A * | 8/1987 | Nishiki et al. | 250/361 R |
| 5,184,018 | A * | 2/1993 | Conrads et al. | 250/370.09 |
| 6,271,880 | B1 | 8/2001 | Kameshima et al. | 348/244 |
| 6,295,142 | B1 | 9/2001 | Watanabe et al. | 358/482 |
| 6,330,303 | B1 | 12/2001 | Yamane et al. | 378/98.8 |
| 6,486,808 | B1 * | 11/2002 | Seppi et al. | 341/139 |
| 6,600,158 | B1 | 7/2003 | Okada et al. | 250/370.11 |
| 6,614,286 | B1 * | 9/2003 | Tang | 327/337 |
| 6,623,990 | B2 | 9/2003 | Watanabe et al. | 438/4 |
| 6,696,687 | B1 * | 2/2004 | Tomisaki et al. | 250/370.09 |
| 6,818,899 | B2 | 11/2004 | Endo | 250/370.14 |
| 7,110,502 | B2 * | 9/2006 | Tsuji | 378/116 |
| 7,126,127 | B2 | 10/2006 | Watanabe et al. | 250/370.01 |
| 2002/0191828 | A1 * | 12/2002 | Colbeth et al. | 382/132 |
| 2006/0138333 | A1 * | 6/2006 | Nascetti et al. | 250/370.09 |
| 2006/0255239 | A1 | 11/2006 | Watanabe et al. | 250/207 |
| 2006/0289769 | A1 | 12/2006 | Yagi et al. | 250/362 |

OTHER PUBLICATIONS

RadiologyInfo, www.radiologyinfo.org/content/chest_radiography.htm, Jul. 9, 2004.*

* cited by examiner

*Primary Examiner*—David P Porta
*Assistant Examiner*—Yara B Green
(74) *Attorney, Agent, or Firm*—Fitzpatrick, Cella, Harper & Scinto

(57) ABSTRACT

A radiation image pickup apparatus or the like which realizes improvement of noise resistance characteristics when adding pixel signals is provided. For this purpose, the radiation image pickup apparatus has a switching unit which is arranged between a signal wiring and an amplifier and can switch electrical connection among a plurality of signal wirings and electrical connection between a predetermined one of the plurality of signal wirings and the amplifier corresponding thereto. In accordance with mode setting, the switching unit switches a first state where the plurality of signal wirings are electrically connected and the predetermined signal wiring and the corresponding amplifier are electrically disconnected and a second state where the plurality of signal wirings are electrically disconnected and the predetermined signal wiring and the corresponding amplifier are electrically connected.

13 Claims, 11 Drawing Sheets

RADIATION IMAGE PICKUP APPARATUS, ITS CONTROL METHOD, AND RADIATION IMAGE PICKUP SYSTEM

BACKGROUND OF THE INVENTION

1. Field of the Invention

The present invention relates to a radiation image pickup apparatus, a radiation image pickup system, a control method of the radiation image pickup apparatus, and a program for allowing a computer to execute the control method. More particularly, the invention relates to a radiation image pickup apparatus having a sensor array constructed by two-dimensionally arranging pixels each including: a conversion element for converting a radiation from an object into an electric signal; and a transfer switching element for transferring the electric signal to an outside.

2. Description of the Related Art

In recent years, there has been known a radiation image pickup apparatus of flat panel type using a sensor array constructed by two-dimensionally arranging pixels each constructed by: a conversion element for converting a radiation into signal charges (electric signal); and a switching element such as a TFT or the like for transferring the electric signal to an outside. In such a flat panel type radiation image pickup apparatus, each of the conversion element and the switching element is made of a material such as amorphous silicon or polysilicon formed as a film on a glass substrate. In the radiation image pickup apparatus, generally, by performing matrix-driving using the switching elements such as TFTs or the like, the signal charges converted by the conversion elements are transferred to a reading circuit unit and read out.

The conventional radiation image pickup apparatus has pixels each including: a photodiode made of amorphous silicon as a conversion element; and a thin film transistor (TFT) as a switching element. The device has a sensor array constructed by two-dimensionally arranging those pixels and performs the matrix-driving. A bias voltage is applied from a power source to a common electrode side of the photodiode of each pixel through a bias line.

The conventional radiation image pickup apparatus in which the area sensor array constructed by two-dimensionally arranging the pixels each having the photodiode and the switching element is read out by the matrix-driving has simply been described above. The radiation image pickup apparatus with such a construction in which the area sensor array is read out by the matrix-driving has been disclosed in, for example, U.S. Pat. No. 6,330,303.

In the conventional radiation image pickup apparatus, there is a case where a technique called "pixel binning" in which the pixels (of a plurality of rows) connected to a same drive wiring are grouped and signals of the group pixels are added and read out is used. It is an object of the pixel adding to accomplish the improvement of a reading speed, adjustment of resolution, an increase in signal amount, and the like. The embodiment about the pixel binning in the horizontal scanning direction has also been disclosed in U.S. Pat. No. 6,330,303.

SUMMARY OF THE INVENTION

First, problems of the invention to be solved will be explained with reference to FIGS. 10 and 11. FIG. 10 is a schematic constructional diagram in the conventional radiation image pickup apparatus for explaining the problems of the invention. FIG. 11 is a timing chart showing the operation of the conventional radiation image pickup apparatus for explaining the problems of the invention.

As shown in FIG. 10, the conventional radiation image pickup apparatus has a sensor array 100 constructed by two-dimensionally arranging pixels 101 and performs matrix-driving. Each pixel 101 has: one of photodiodes (e.g. S11) made of amorphous silicon serving as conversion elements; and one of thin film transistors (TFTs) (e.g. T11) as switching elements. A bias voltage Vs has been applied from a power source 300 to common electrode sides of the PIN type photodiodes of each pixel 101 through a bias line 102.

Gate electrodes of the switching elements of each pixel 101 in row direction are connected to common drive wirings Vg1 to Vg4. The drive wirings Vg1 to Vg4 are connected to a gate driving device 400 constructed by a shift register or the like. Source electrodes of the switching elements in column direction are connected to common signal wirings Sig1 to Sig4. Signal charges of each pixel 101 are converted into analog signals by a reading circuit unit 200 through the signal wirings Sig1 to Sig4. The reading circuit unit 200 is constructed by amplifiers A1 to A4, an analog multiplexer 201, a buffer amplifier 202, and the like. The analog signals converted by the reading circuit unit 200 are converted into digital signals by an A/D converter 500. The digital signals are processed by an image processing unit 600 constructed by a memory, a processor, and the like and outputted to a monitor (not shown) or stored in a recording apparatus such as a hard disk or the like.

The operation of the conventional radiation image pickup apparatus will now be described with reference to FIGS. 10 and 11.

First, reset switches $SW_{RC}$ provided for the amplifiers A1 to A4 are turned on by a reset signal RC which is generated from a timing generator (not shown). Thus, integration capacitors Cf of the amplifiers A1 to A4 and the signal wirings Sig1 to Sig4 are reset.

Subsequently, a pulse is applied to the drive wiring Vg1 and the switching elements connected to the drive wiring Vg1 are turned on. Thus, the signal charges generated in the photodiodes are transferred to the reading circuit unit 200 through the signal wirings Sig1 to Sig4. The transferred signal charges are converted into voltages by the amplifiers A1 to A4 connected to the signal wirings Sig1 to Sig4.

Subsequently, sampling and holding signals SH are applied to the reading circuit unit 200 from the timing generator (not shown), so that the output voltages from the amplifiers A1 to A4 are sampled and held into sampling and holding capacitors $C_{SH}$. After that, the voltages which have been sampled and held in the S/H capacitors $C_{SH}$ are converted into serial voltages by the analog multiplexer 201 synchronously with a clock MUX_CLK from the timing generator (not shown). The converted serial voltages are inputted as analog signals to the A/D converter 500 through the buffer amplifier 202. The analog signals inputted to the A/D converter 500 are A/D converted and supplied as digital signals to the image processing unit 600 in accordance with resolution of the A/D converter 500.

Subsequently, a pulse is applied to the drive wiring Vg2 and the switching elements (T21 to T24) connected to the drive wiring Vg2 are turned on. Thus, the signal charges generated in the photodiodes S21 to S24 are read out to the reading circuit unit 200 through the signal wirings Sig1 to Sig4. Operations similar to those mentioned above are also repetitively executed to the drive wiring Vg3 and Vg4 and the signal charges in the photodiodes of the whole sensor array 100 are read out.

Although irradiating timing of light (or X-ray) is not mentioned in the above description, either continuous light (or continuous X-ray) or pulse light (or pulse X-ray) may be used fundamentally.

In the conventional radiation image pickup apparatus, there is a case where the technique called "pixel binning" in which the pixels connected to a same drive wiring are grouped and signals of the group pixels are added and read out is used. It is an object of the pixel adding to accomplish the improvement of the reading speed, the adjustment of the resolution, the increase in signal amount, or the like. The embodiment about the pixel binning in the horizontal scanning direction has also been disclosed in U.S. Pat. No. 6,330,303.

That is, the following constructions (1) to (3) are specifically shown in U.S. Pat. No. 6,330,303.

(1) The signals derived after the amplifiers connected to the signal wirings are added by using an adding circuit of an operational amplifier.

(2) The digital signals which were A/D converted by the A/D converter are digitally added by the image processing unit.

(3) For the signals derived after the amplifiers connected to the signal wirings, an amplification factor is changed in accordance with a photographing mode.

However, it should be noted that the addition of the signals is performed after the outputs of the amplifiers in U.S. Pat. No. 6,330,303.

In such a radiation image pickup apparatus, since the analog signals after the amplifiers are added, there is a fear that noises of the amplifiers, noises of the adding circuit (addition of thermal noises of resistors and amplifiers constructing the adding circuit), and the like are multiplexed to the added signal. There is also a fear of a case where a variation in gains of the amplifiers connected to the signal wirings and the like become noise components in the added signal. In the case where the digital signals which were A/D converted by the A/D converter are digitally added, there is also a fear that a quantization error of the A/D converter is added.

That is, U.S. Pat. No. 6,330,303 has such a problem that when the pixel signals are added, nothing is considered with respect to a deterioration in characteristics due to the noises in the amplifiers or the noises in the adding circuit or a deterioration in characteristics due to the quantization noises of the A/D converter. Therefore, U.S. Pat. No. 6,330,303 has such a problem that the noises are multiplexed and noise resistance characteristics cannot be improved.

According to the pixel addition in the radiation image pickup apparatus, as compared with a non-addition method, the improvement of the reading speed, the adjustment of the resolution, the increase in signal amount according to the radiation of a small dose, and the like can be accomplished. That is, it is very useful in a radiation image pickup apparatus which can perform a motion image photography such as a radioscopy or the like in which a high reading speed, the radiation of a small dose, and high sensitivity are required. However, according to U.S. Pat. No. 6,330,303, when the pixel signals are added, there is a deterioration in characteristics due to the noises in the amplifiers, the noises in the adding circuit, or the quantization noises of the A/D converter. Therefore, in the radiation image pickup apparatus which can perform the motion image photography, according to the pixel addition disclosed in U.S. Pat. No. 6,330,303, there is a fear that the advantage of the pixel addition is decreased by the deterioration in characteristics due to the noises as mentioned above.

It is, therefore, an object of the invention to provide a radiation image pickup apparatus, a radiation image pickup system, a control method of the radiation image pickup apparatus, and a program for such a control method, in which when pixel signals are added, the improvement of noise resistance characteristics is realized.

According to the invention, there is provided a radiation image pickup apparatus comprising: a sensor array constructed by two-dimensionally arranging a plurality of pixels each having a conversion element for converting a radiation into an electric signal and a transfer switching element for transferring the electric signal to an outside; a plurality of signal wirings each adapted to connect the transfer switching elements of the pixels of the sensor array in a column direction; a reading circuit unit including a plurality of amplifiers which are provided in correspondence to said signal wirings and each of which amplifies said electric signal transferred from each of said transfer switching elements and reads out the amplified signal; a mode setting unit adapted to set a mode in the radiation image pickup apparatus; and a switching unit which can switch electrical connection among the plurality of signal wirings and electrical connection between a predetermined one of the plurality of signal wirings and the amplifier corresponding thereto, wherein the switching unit is arranged between the signal wiring and the amplifier and, in accordance with the setting of the mode, the switching unit switches a first state where the plurality of signal wirings are electrically connected and the predetermined signal wiring and the amplifier corresponding thereto are electrically disconnected and a second state where the plurality of signal wirings are electrically disconnected and the predetermined signal wiring and the amplifier corresponding thereto are electrically connected.

According to the invention, there is provided a control method for a radiation image pickup apparatus, comprising: a first step of setting a mode in the radiation image pickup apparatus including a sensor array constructed by two-dimensionally arranging a plurality of pixels each having a conversion element for converting a radiation into an electric signal and a transfer switching element for transferring the electric signal to an outside, a plurality of signal wirings each adapted to connect the transfer switching elements of the pixels of the sensor array in a column direction, a reading circuit unit including a plurality of amplifiers which are provided in correspondence to said signal wirings and each of which amplifies said electric signal transferred from each of said transfer switching elements and reads out the amplified signal, and a switching unit which can switch electrical connection among the plurality of signal wirings and electrical connection between a predetermined one of the plurality of signal wirings and the amplifier corresponding thereto; and a second step of switching a state of the switching unit on the basis of the setting of the mode in the first step to either a first state where the plurality of signal wirings are electrically connected and the predetermined signal wiring and the amplifier corresponding thereto are electrically disconnected or a second state where the plurality of signal wirings are electrically disconnected and the predetermined signal wiring and the amplifier corresponding thereto are electrically connected.

Further features of the present invention will become apparent from the following description of exemplary embodiments described with reference to the attached drawings.

DESCRIPTION OF THE EMBODIMENTS

Preferred embodiments of the invention will be described hereinbelow with reference to the drawings. Although examples in which an X-ray is used as a radiation are shown in the embodiments of the invention, the radiation in the invention is not limited to the X-ray but other electromagnetic waves such as $\alpha$-ray, $\beta$-ray, $\gamma$-ray, and the like are also incorporated.

First Embodiment

Figure 1:
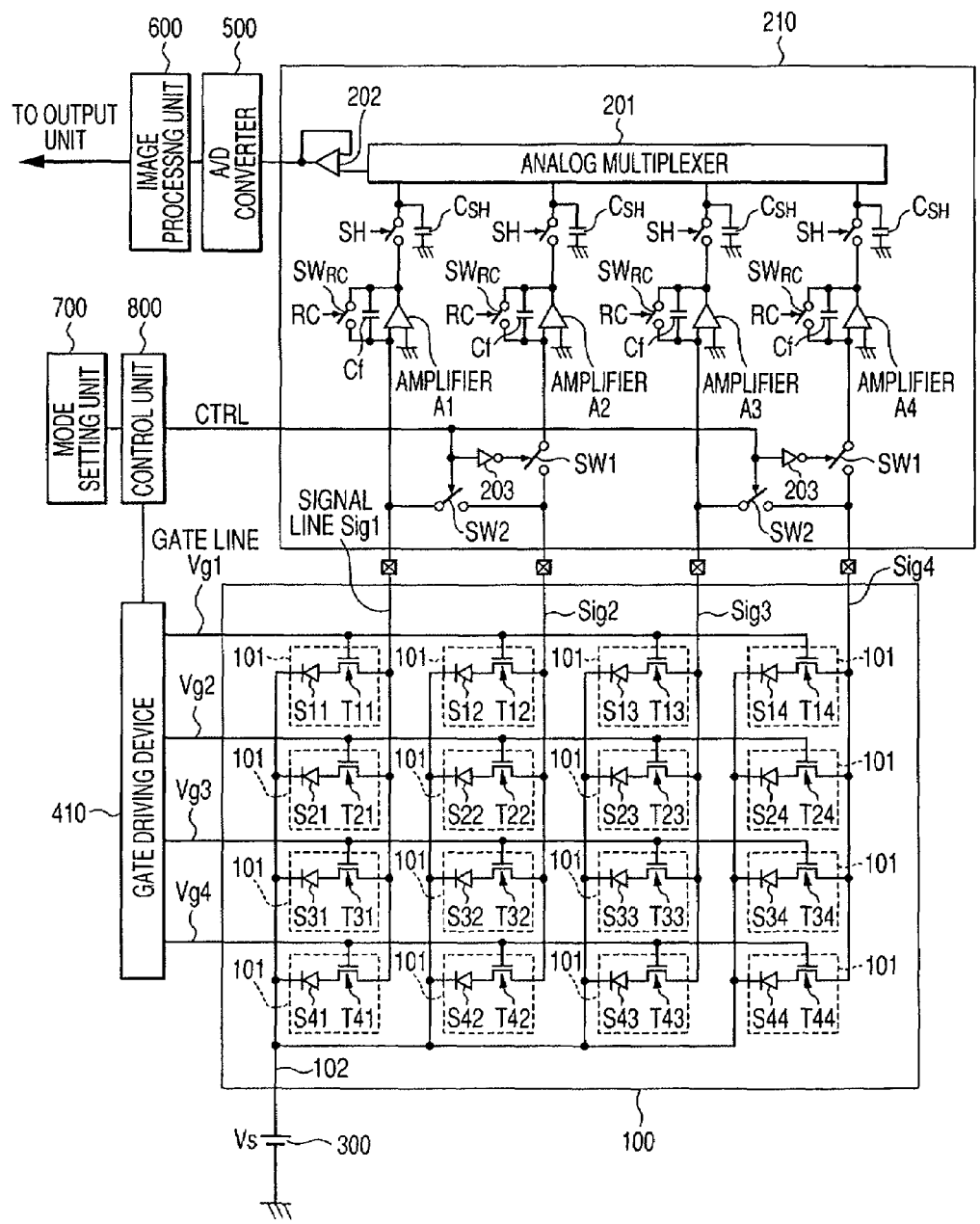
FIG. 1 is a schematic constructional diagram of a radiation image pickup apparatus according to the first embodiment of the invention.

FIG. 1 is a schematic constructional diagram of a radiation image pickup apparatus according to the first embodiment of the invention.

As shown in FIG. 1, the radiation image pickup apparatus according to the first embodiment has: the sensor array 100; a reading circuit unit 210; the power source 300; a gate driving device 410; the A/D converter 500; the image processing unit 600; a mode setting unit 700; and a control unit 800.

The sensor array 100 is constructed by two-dimensionally arranging the pixels 101 and performs the matrix-driving. Each pixel 101 has: one of the photodiodes (e.g. S11) made of amorphous silicon corresponding to the conversion elements each for converting the radiation into the electric signal; and one of the thin film transistors (TFTs) (e.g. T11) corresponding to the transfer switching elements each for transferring the electric signal of each photodiode to the outside. The bias voltage Vs has been applied from the power source 300 to the common electrode sides of the photodiodes of each pixel 101 through the bias line 102.

The gate electrodes of the TFTs of each pixel 101 are connected to the common drive wirings Vg1 to Vg4 every row of each pixel. The drive wirings Vg1 to Vg4 are connected to the gate driving device 410 constructed by the shift register or the like. The source electrodes of the TFTs of each pixel 101 are connected to the common signal wirings Sig1 to Sig4 every column of each pixel. The signal charges as an electric signal in each pixel 101 are converted into the analog signals by the reading circuit unit 210. The reading circuit unit 210 has the amplifiers A1 to A4, the analog multiplexer 201, the buffer amplifier 202, and the like. The analog signals converted by the reading circuit unit 210 are converted into the digital signals by the A/D converter 500. The digital signals are processed by the image processing unit 600 constructed by the memory, the processor, and the like and outputted to the monitor (not shown) or stored in the recording apparatus such as a hard disk or the like.

The amplifiers A1 to A4 are provided in correspondence to the signal wirings Sig1 to Sig4, amplify the signal charges transferred from the TFTs, and read out the amplified signal charges. The gate driving device 410 drives the drive wirings Vg1 to Vg4 under the control of the control unit 800 in order to read out the signal charges of each pixel 101 connected to the drive wirings Vg1 to Vg4.

Figure 10:
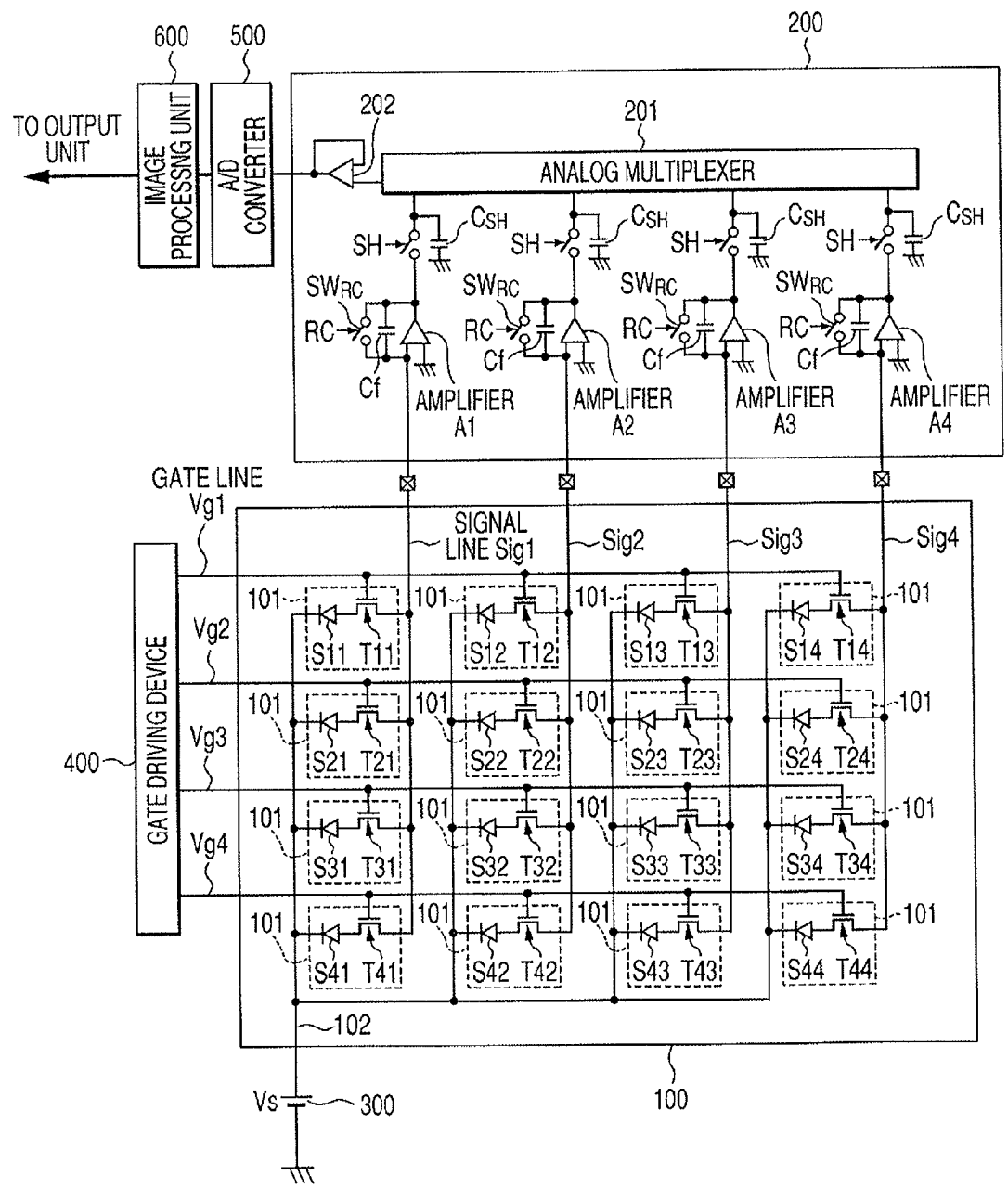
FIG. 10 is a schematic constructional diagram of a radiation image pickup apparatus for explaining problems in the invention.

As compared with the general device shown in FIG. 10, the radiation image pickup apparatus according to the first embodiment further has first switches SW1, second switches SW2, and an inverter 203 in the reading circuit unit 210. Each switching unit is constructed by the first switch SW1, the second switch SW2, and the inverter 203. Further, the radiation image pickup apparatus has the mode setting unit 700 and the control unit 800.

The first switch SW1 switches the electrical connection and the electrical disconnection between the signal wiring and the amplifier provided in correspondence to the signal wiring. In the embodiment, the first switches SW1 are provided between the signal wirings Sig2 and Sig4 of the even-number columns and the amplifiers A2 and A4, respectively.

The second switch SW2 switches the electrical connection and the electrical disconnection among the plurality of (in the embodiment, two) different signal wirings. In the embodiment, as second switches SW2, there are provided switches for switching the electrical connection and the electrical disconnection between the signal wiring Sig1 of the odd-number column and the signal wiring Sig2 of the even-number column and between the signal wiring Sig3 of the odd-number column and the signal wiring Sig4 of the even-number column. The second switch SW2 is arranged so as to be connected between the signal wiring and the amplifier. That is, it is arranged so as to connect the input stages of the amplifiers of a plurality of different signal wirings. Further, the second switch SW2 is arranged at a position (the input stage of the first switch SW1) closer to the pixel than that to the first switch SW1. Although the second switch SW2 is constructed by the switch adapted to switch the electrical connection and the electrical disconnection between the two different signal wirings in the embodiment, in the invention, it is sufficient to use the switch which can switch the electrical connection and the electrical disconnection among a plurality of different signal wirings. For example, the second switch SW2 may be constructed so as to switch the electrical connection and the electrical disconnection among four signal wirings.

A switch unit switches the electrical connection and the electrical disconnection between the first switch SW1 and the second switch SW2 on the basis of a control signal from the control unit 800.

The mode setting unit 700 sets the mode in the radiation image pickup apparatus by switching a "normal reading mode" for reading out the electric signal from one pixel by the amplifier corresponding to the pixel and a "pixel binning mode" for adding the electric signals from a plurality of pixels and reading out the added electric signal by one of a plurality of amplifiers corresponding to each pixel. The mode setting unit 700 outputs a mode signal indicative of the set mode to the control unit 800.

The control unit 800 is connected to the mode setting unit 700, the reading circuit unit 210, and the gate driving device 410. On the basis of the setting of the mode by the mode setting unit 700, the control unit 800 controls the switch unit, thereby controlling the change-over of the first switch SW1 and the second switch SW2.

Specifically speaking, if the mode signal indicative of the setting of the "normal reading mode" is received from the mode setting unit 700, the control unit 800 controls the inverter 203 so as to electrically connect the first switch SW1 and electrically disconnect the second switch SW2. If the mode signal indicative of the setting of the "pixel binning mode" is received from the mode setting unit 700, the control unit 800 controls the inverter 203 so as to electrically disconnect the first switch SW1 and electrically connect the second switch SW2.

When the signal charges of each pixel 101 connected to the drive wirings Vg1 to Vg4 are read out, the control unit 800 controls the gate driving device 410 so as to drive the drive wirings Vg1 to Vg4 and scan.

The operation of the radiation image pickup apparatus according to the embodiment will now be described.

Figure 2:
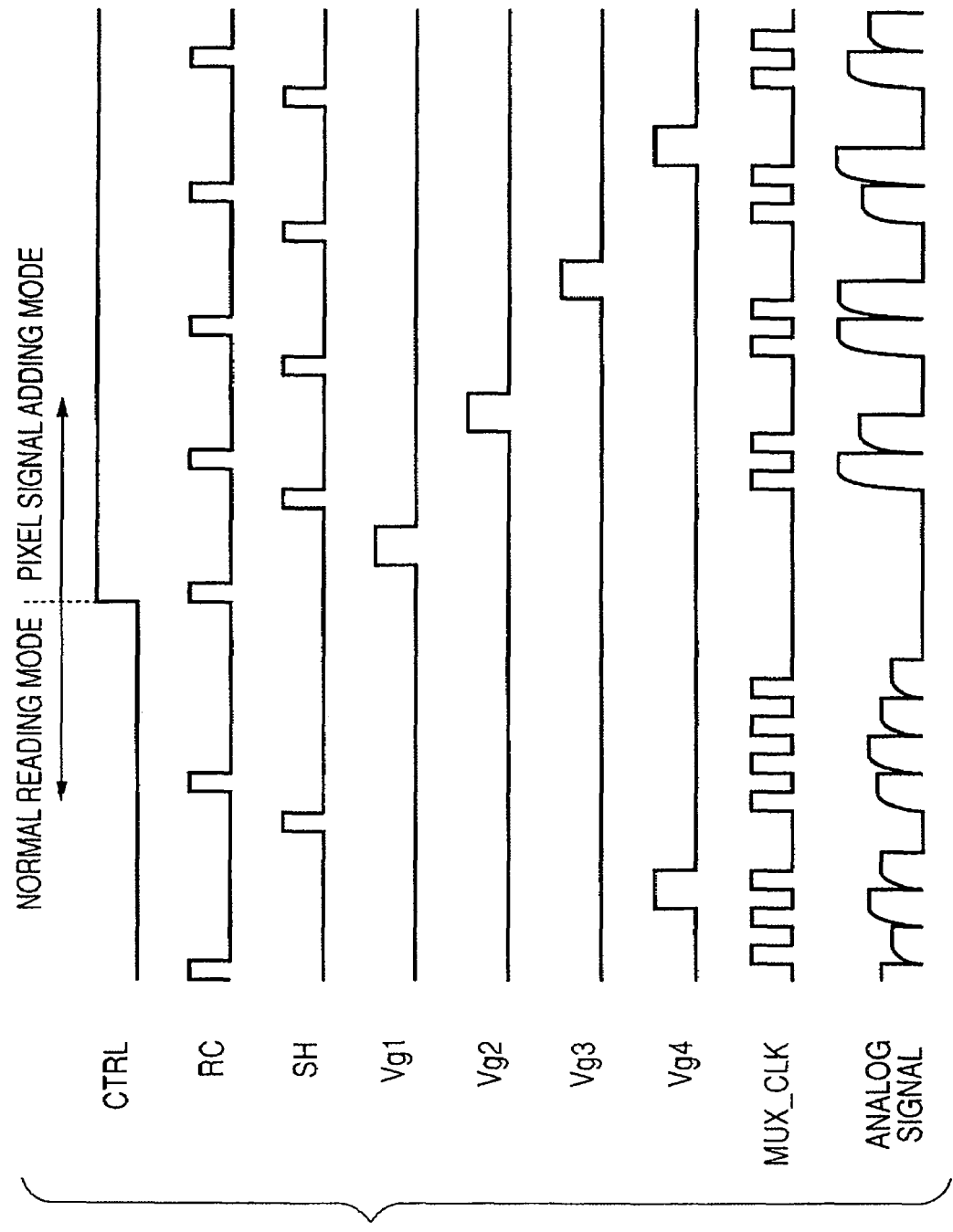
FIG. 2 is a timing chart showing the operation of the radiation image pickup apparatus according to the first embodiment of the invention.

FIG. 2 is a timing chart showing the operation of the radiation image pickup apparatus according to the first embodiment of the invention.

First, the reset switches $SW_{RC}$ provided for the amplifiers A1 to A4 are turned on by the reset signal RC which is generated from the timing generator (not shown) and the integration capacitors Cf of the amplifiers A1 to A4 and the signal wirings Sig1 to Sig4 are reset.

Figure 11:
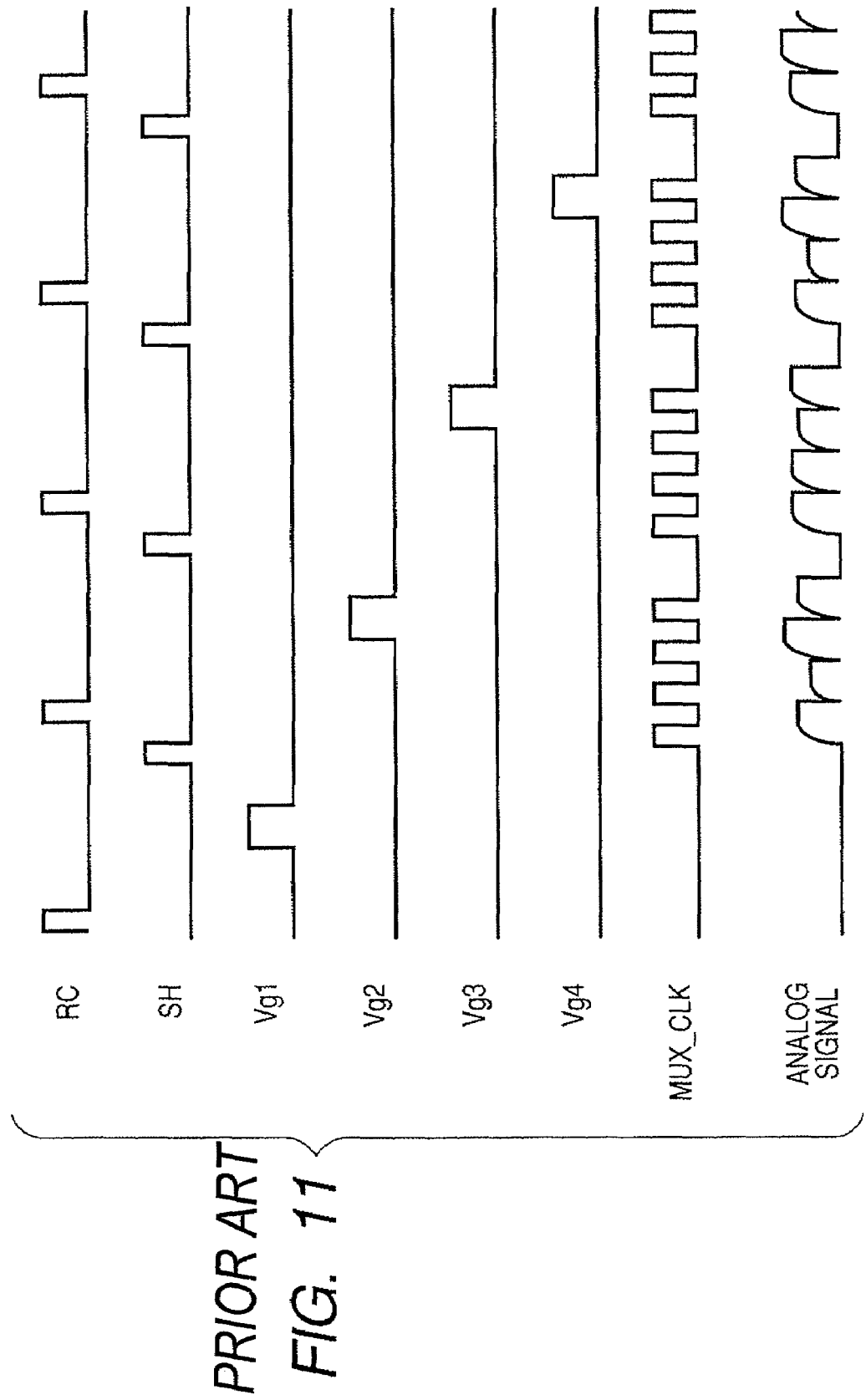
FIG. 11 is a timing chart showing the operation of the radiation image pickup apparatus for explaining the problems in the invention.

When the "normal reading mode" is set by the mode setting unit 700, the control unit 800 outputs a control signal CTRL (specifically speaking, an "L" signal in the embodiment) regarding the "normal reading mode" to the switch unit. The switch unit which received the control signal CTRL electrically connects the first switch SW1 and electrical disconnects the second switch SW2. The operation in the "normal reading mode", is similar to that shown in FIG. 11. That is, the signal charges of each pixel 101 are sent to the amplifiers A1 to A4 provided in correspondence to the signal wirings through the signal wirings Sig1 to Sig4 and converted into voltages here.

Subsequently, when the "pixel binning mode" is set by the mode setting unit 700, the control unit 800 outputs the control signal CTRL (specifically speaking, an "H" signal in the embodiment) regarding the "pixel binning mode" to the switch unit. The s switch unit which received the control signal CTRL electrically disconnects the first switch SW1 and electrical connects the second switch SW2. In this instance, the signal charges in the pixels connected to the signal wirings Sig2 and Sig4 of the even-number columns are added to the signal charges in the pixels connected to the signal wirings Sig1 and Sig3 of the odd-number columns by the second switches SW2, respectively. The added signal charges are converted into voltages by the amplifiers A1 and A3 of the odd-number columns, respectively.

In the first embodiment, in the "pixel binning mode", the signal charges in the pixels of the even-number columns and the signal charges in the pixels of the odd-number columns are added in front of the amplifiers A1 to A4 (before the input stage) and the added signal charges are read out by the amplifiers A1 and A3 of the odd-number columns. Thus, when the pixel signals are added, as compared with the case where the adding circuit is provided after the amplifiers A1 to A4 or the case where the they are A/D converted by the A/D converter 500 and, thereafter, digitally added, the occurrence of the noise multiplex due to the noises in the amplifiers A1 to A4, the noises in the adding circuit, the quantization noises of the A/D converter, or the like can be prevented. As compared with the general radiation image pickup apparatus, the improvement of the noise resistance characteristics can be realized. Particularly, in the radiation image pickup apparatus which can perform the motion image photography in which the high reading speed, the radiation of a small dose, and the high sensitivity are required, since the reduction in advantage of the pixel addition can be prevented, the effect of the invention becomes more typical.

Since it is sufficient that the reading circuit unit 210 executes the scan in the horizontal direction, that is the scan of the analog multiplexer 201 only to the signal wirings Sig1 and Sig3 of the odd-number columns, the reading speed can be also improved. Such an effect is particularly remarkable in the case where an ON time in each of the switching elements of each pixel 101 is shorter than the time necessary for the horizontal scan, in other words, in the case where the reading speed of the radiation image pickup apparatus is rate limited by the horizontal scan.

A cross sectional structure of the radiation image pickup apparatus according to the embodiment will now be described.

Figure 3:
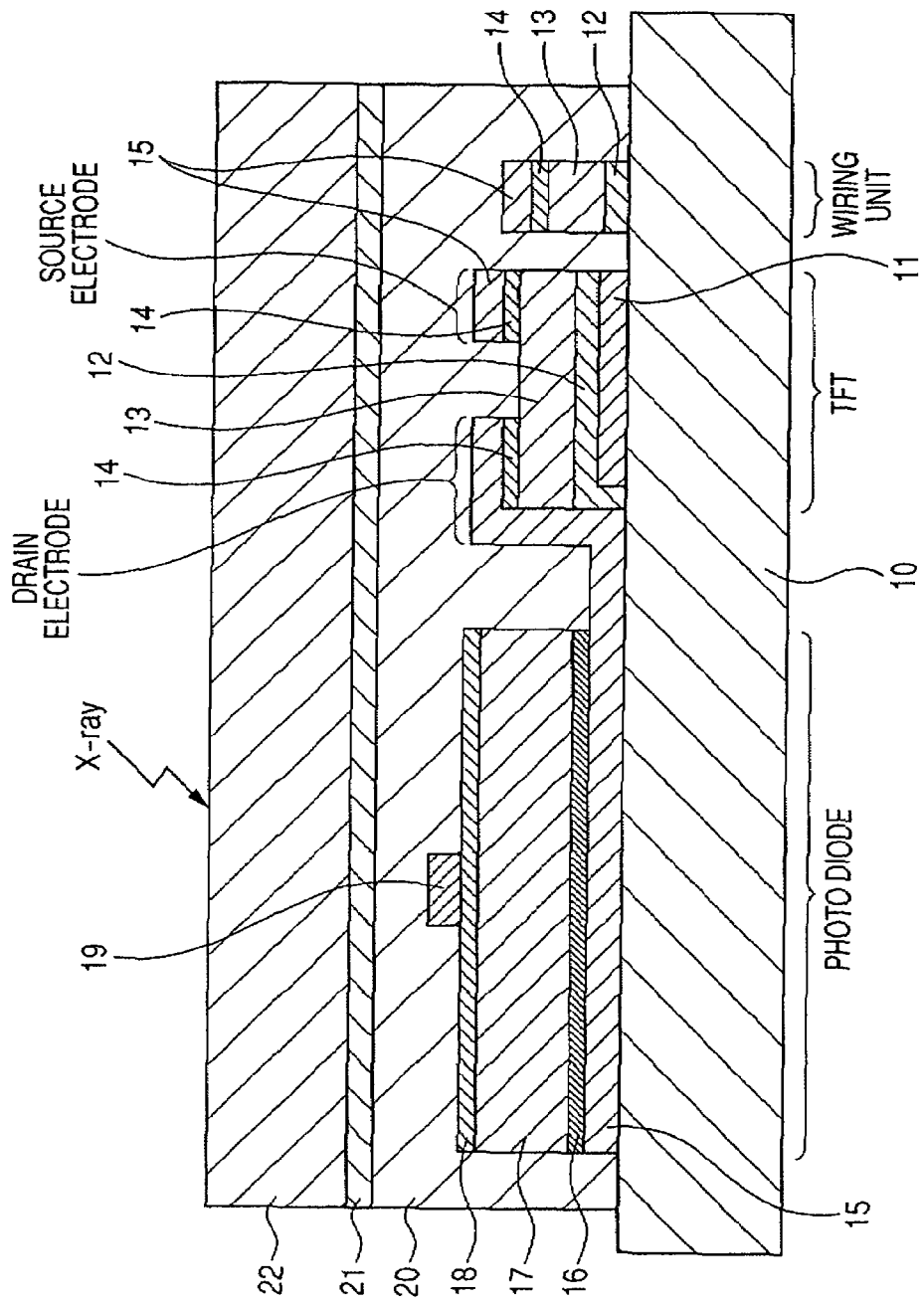
FIG. 3 is a schematic cross sectional view of a pixel in a sensor array.

FIG. 3 is a schematic cross sectional view of the pixel in the sensor array. As shown in FIG. 3, each pixel 101 is constructed by forming the photodiode as a conversion element, the TFT as a switching element, and a wiring unit onto a glass substrate 10 as an insulating substrate.

The TFT is constructed by laminating the following layers onto the glass substrate 10: a first metal thin film layer 11 serving as a gate electrode; an insulating layer 12 made of an amorphous silicon nitride film formed on the first metal thin film layer 11; a semiconductor layer 13 made of amorphous silicon formed on the insulating layer 12; n-type impurity semiconductor layers (n-layers) 14 separately formed in a source forming region and a drain forming region on the semiconductor layer 13, respectively; and second metal thin film layers 15 formed in a source forming region and a drain forming region on the n-layers 14 and serving as a source electrode and a drain electrode, respectively.

The photodiode is constructed by laminating the following layers onto the glass substrate 10: the second metal thin film layer 15 connected to the drain electrode of the TFT and serving as a lower electrode layer; a p-type impurity semiconductor layer (p-layer) 16 formed on the second metal thin film layer 15; a semiconductor layer 17 made of amorphous silicon formed on the p-layer 16; an n-type impurity semiconductor layer (n-layer) 18 formed on the semiconductor layer 17; and a third metal thin film layer 19 formed on the n-layer 18 and serving as an upper electrode layer.

The wiring unit is constructed by laminating the following layers: the insulating layer 12 made of the amorphous silicon nitride film formed on the glass substrate 10; the semiconductor layer 13 made of amorphous silicon formed on the insulating layer 12; the n-type impurity semiconductor layer (n-layer) 14 formed on the semiconductor layer 13; and the second metal thin film layer 15 formed on the n-layer 14 and serving as a wiring layer.

A protecting layer 20 made of the amorphous silicon nitride film or the like is provided over the photodiode, TFT, and wiring unit formed as films on the glass substrate 10 and the whole portions are covered with the protecting layer 20. Since FIG. 3 shows an example in the case of constructing an X-ray image pickup device using the X-ray as a radiation, a phosphor layer 22 as a wavelength converter is further arranged over the protecting layer 20 through an adhesive layer 21.

Generally, the photodiode made of amorphous silicon as a main material is hardly sensitive to the X-ray. Therefore, as shown in FIG. 3, it is necessary that the photodiode is provided with the phosphor layer 22 as a wavelength converter to convert the X-ray into visible light is provided over the protecting layer 20 through the adhesive layer 21. As a phosphor layer 22, a layer made of gadolinium system or CsI (cesium iodide) as a main material is grown to a columnar crystal and such a crystal or the like is used.

When the X-ray transmitted through the object enters the phosphor layer 22, the X-ray is converted into the visible light in the phosphor layer 22 and enters the photodiode. The signal charges generated in the semiconductor layer 17 of the photodiode are sequentially transferred to the reading circuit unit 210 by the TFT and read out.

Although the embodiment has been described with respect to the example in which the PIN-type photodiode made of amorphous silicon as a main material is used as a photoelectric conversion element, the invention is not limited to such an example. For instance, an MIS-type sensor or an element made of polysilicon as a main material can be also used as a photoelectric conversion element. A conversion element of what is called a direct converting type for absorbing the radiation such as an X-ray or the like and directly converting it into charges can be also used as a photoelectric conversion element. As a conversion element of the direct converting type in this case, there can be mentioned an element made of at least one of amorphous selenium, gallium arsenide, gallium phosphide, lead iodide, mercury iodide, CdTe, and CdZnTe as a main material.

Although the embodiment has been described with respect to the example in which a transistor obtained by forming amorphous silicon as a main material onto the glass substrate 10 is used as a TFT, the invention is not limited to such an example. For instance, a transistor made of polysilicon or an organic material as a main material can be also used.

Each device of the reading circuit unit 210 is generally constructed by an integrated circuit (IC) made of polysilicon as a main material. That is, together with the amplifiers A1 to A4, the analog multiplexer 201, and the like, the first switch SW1, the second switch SW2, and the switch change-over unit 203 are constructed on the insulating substrate in the integrated circuit made of polysilicon as a main material. Although each device of the reading circuit unit 210 is made of polysilicon as a main material in the embodiment, the invention is not limited to such an example. For instance, it may be made of amorphous silicon as a main material. It may be formed on a monocrystalline semiconductor substrate.

In the embodiment, the gate driving device 410 may be constructed by a shift register including the TFT made of amorphous silicon or polysilicon as a main material on the same glass substrate 10 as that of the TFT of the sensor array 100. According to such a construction, since there is no need to separately provide the gate driving device 410, such an effect is particularly remarkable for the cost reduction of the radiation image pickup apparatus.

Second Embodiment

A schematic construction of a radiation image pickup apparatus according to the second embodiment of the invention is similar to that of the radiation image pickup apparatus according to the first embodiment shown in FIG. 1.

In addition to the functions described in the first embodiment, if the mode signal indicative of the setting of the "pixel binning mode" is received from the mode setting unit 700, the control unit 800 in the second embodiment controls the gate driving device 410 so as to simultaneously drive some of the drive wirings Vg1 to Vg4 and scan. That is, in the "pixel binning mode", not only the addition of the pixel signals in the horizontal scanning direction but also the addition of the pixel signals in the vertical scanning direction is simultaneously executed.

Figure 4:
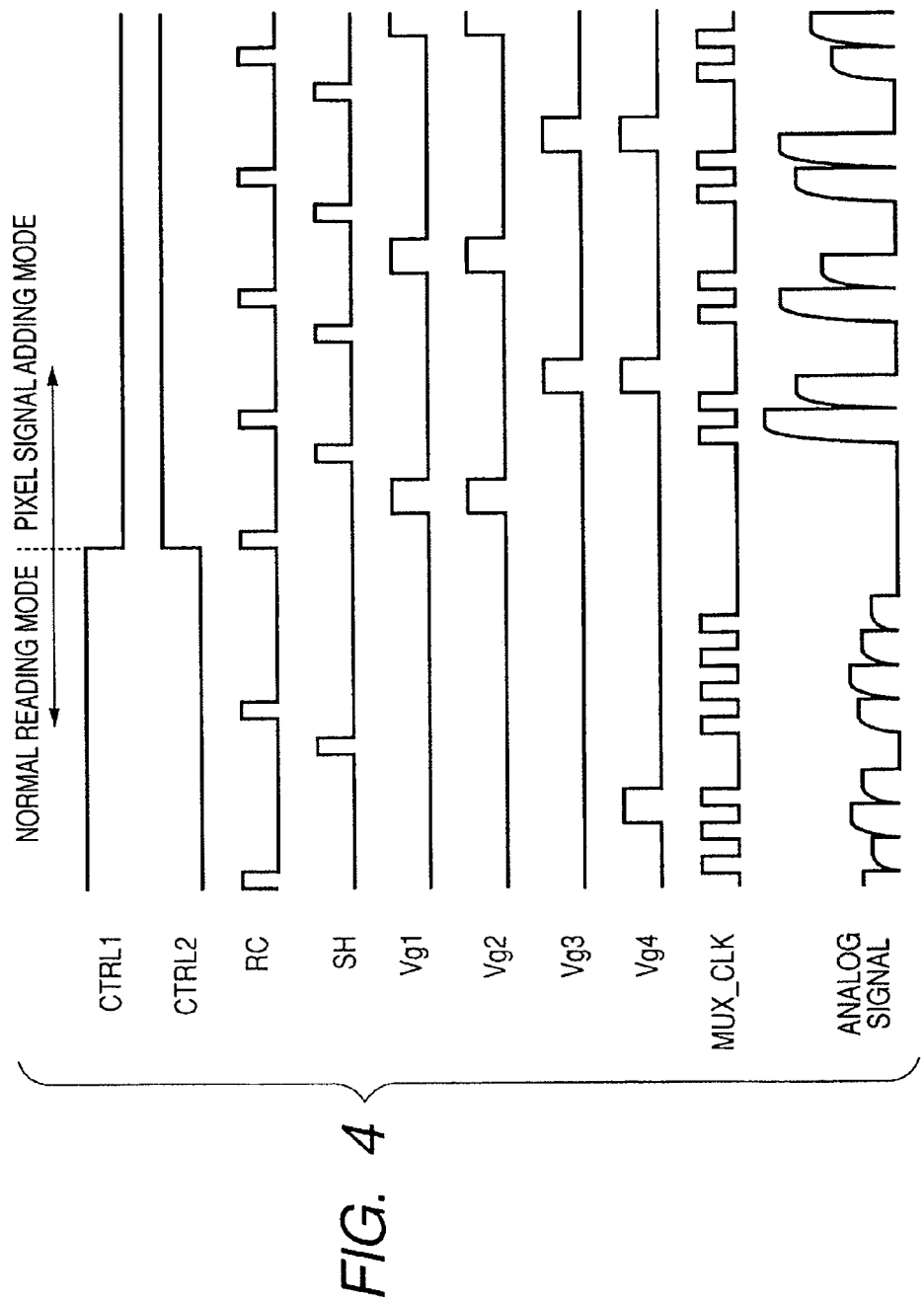
FIG. 4 is a timing chart showing the operation of a radiation image pickup apparatus according to the second embodiment of the invention.

FIG. 4 is a timing chart showing the operation of the radiation image pickup apparatus according to the second embodiment of the invention. A control signal CTRL1 shown in FIG. 4 is a control signal which is supplied from the control unit 800 shown in FIG. 1 to the gate driving device 410. A control signal CTRL2 shown in FIG. 4 is a control signal (control signal CTRL shown in FIG. 1) which is supplied from the control unit 800 to the switch change-over unit 203. FIG. 4 shows the state where the gate driving device 410 has simultaneously driven the drive wirings Vg1 and Vg2 and has simultaneously driven the drive wirings Vg3 and Vg4 by the control signal CTRL1.

In the second embodiment, resolution in the horizontal direction and resolution in the vertical direction can be made coincide. In the example shown in FIG. 4, the signal charges of four pixels are added at the front stage of the amplifiers A1 to A4. Therefore, as compared with the case where the adding circuit is provided after the amplifiers A1 to A4 or the case where the signal charges are A/D converted by the A/D converter 500 and, thereafter, digitally added, the occurrence of the noise multiplex due to the noises in the amplifiers A1 to A4, the noises in the adding circuit, the quantization noises of the A/D converter, or the like can be prevented. Thus, the noise resistance characteristics can improved and, further, not only the horizontal scanning time but also the vertical scanning time can be shortened. Therefore, the reading speed can be raised.

The embodiment has been described with respect to the example in which the gate driving device 410 simultaneously drives the drive wirings Vg1 and Vg2 and simultaneously drives the drive wirings Vg3 and Vg4 by the control of the control unit 800. However, in the invention, it is sufficient to use a construction in which some of the drive wirings Vg1 to Vg4 are simultaneously driven, for example, the four drive wirings Vg1 to Vg4 may be simultaneously driven.

A cross sectional structure of the radiation image pickup apparatus according to the second embodiment is similar to that of the first embodiment. The gate driving device 410 in the embodiment which can simultaneously scan a plurality of drive wirings may be constructed by a TFT or the like made of amorphous silicon or polysilicon as a main material on the same glass substrate 10 as that of the TFT of the sensor array 100. For example, in the case of forming the gate driving device 410 by the TFT made of polysilicon as a main material, it is possible to form the gate driving device 410 by a method whereby after amorphous silicon was deposited, a process such as laser annealing or the like is performed to amorphous silicon so that it is converted into polysilicon. By forming the gate driving device 410 onto the same glass substrate 10 as that of the TFT of the sensor array 100 as mentioned above, there is no need to separately provide the gate driving device. Therefore, such an effect is particularly remarkable for the cost reduction of the radiation image pickup apparatus.

Third Embodiment

Figure 5:
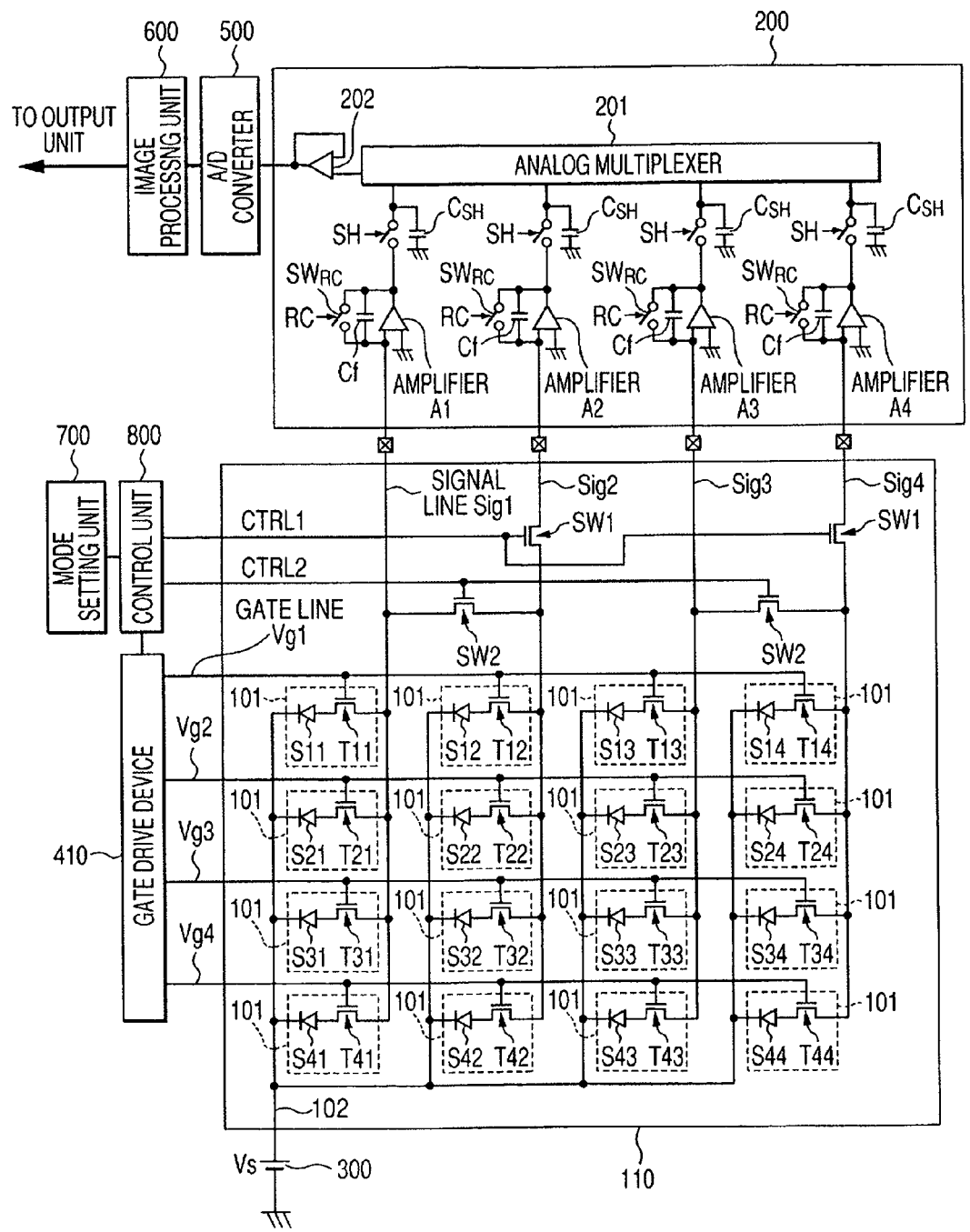
FIG. 5 is a schematic constructional diagram of a radiation image pickup apparatus according to the third embodiment of the invention.

FIG. 5 is a schematic constructional diagram of a radiation image pickup apparatus according to the third embodiment of the invention.

As compared with the radiation image pickup apparatus according to the first embodiment of the invention shown in FIG. 1, in the radiation image pickup apparatus according to the third embodiment, the first switches SW1 and the second switches SW2 are formed on the same insulating substrate (glass substrate 10) as that of the pixels 101 having the photodiodes and the TFTs.

Each of the first switch SW1 and the second switch SW2 is made of amorphous silicon or polysilicon as a main material in a manner similar to each of the TFTs of a sensor array 110. For example, in the case of forming the first switch SW1 and the second switch SW2 by polysilicon as a main material, it is also possible to use a method whereby after amorphous silicon was deposited, a process such as laser annealing or the like is performed to amorphous silicon so that it is converted into polysilicon. The operation of the radiation image pickup apparatus according to the third embodiment is similar to that of the radiation image pickup apparatus according to the first embodiment or the second embodiment.

Fourth Embodiment

Figure 6:
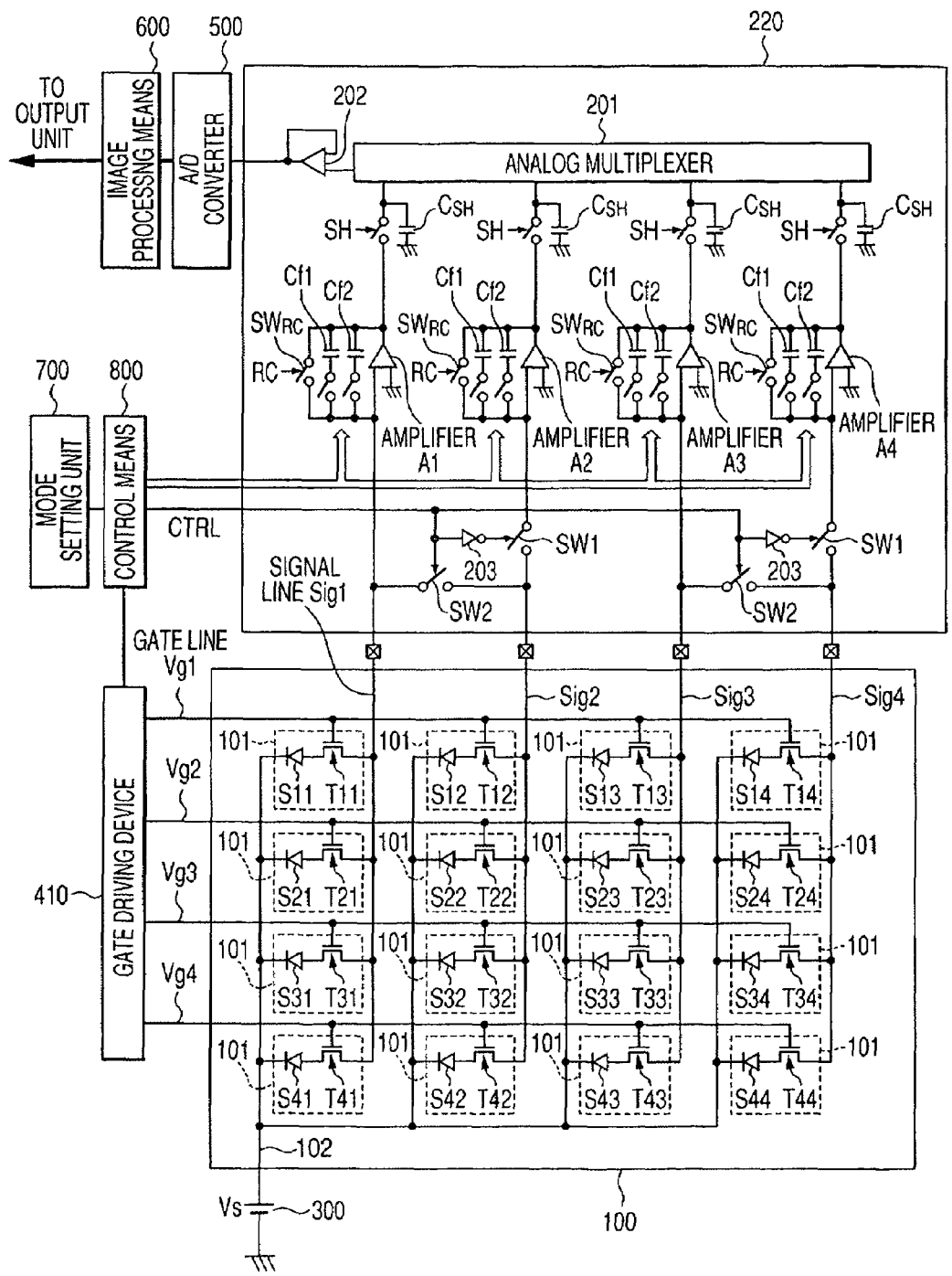
FIG. 6 is a schematic constructional diagram of a radiation image pickup apparatus according to the fourth embodiment of the invention.

FIG. 6 is a schematic constructional diagram of a radiation image pickup apparatus according to the fourth embodiment of the invention.

As compared with the integration capacitors Cf of the amplifiers A1 to A4 of the radiation image pickup apparatus according to the first embodiment shown in FIG. 1, the radiation image pickup apparatus according to the fourth embodiment of the invention has two integration capacitors Cf1 and Cf2 of different capacitance values (it is assumed that Cf1<Cf2). In accordance with the setting of the mode by the mode setting unit, the control unit 800 changes the integration capacitors Cf1 and Cf2 for accumulating the signal charges of the pixel 101.

In the "pixel binning mode", a larger amount of signal charges than that in the "normal reading mode" are transferred to the amplifiers A1 to A4. A dynamic range of each of the amplifiers depends on the integration capacitor Cf. In order to prevent the saturation of the amplifier in the "pixel binning mode" and assure the dynamic range characteristics of the radiation image pickup apparatus, it is desirable to use the construction in which the integration capacitors Cf of the amplifiers can be switched in accordance with the mode.

For this purpose, if the "normal reading mode" is set by the mode setting unit 700, the control unit 800 controls so as to accumulate the signal charges of the pixel 101 into the integration capacitor Cf1. If the "pixel binning mode" is set by the mode setting unit 700, the control unit 800 controls so as to accumulate the signal charges of the pixel 101 into the integration capacitor Cf2 whose capacitance is larger than that of the integration capacitor Cf1.

Figure 7:
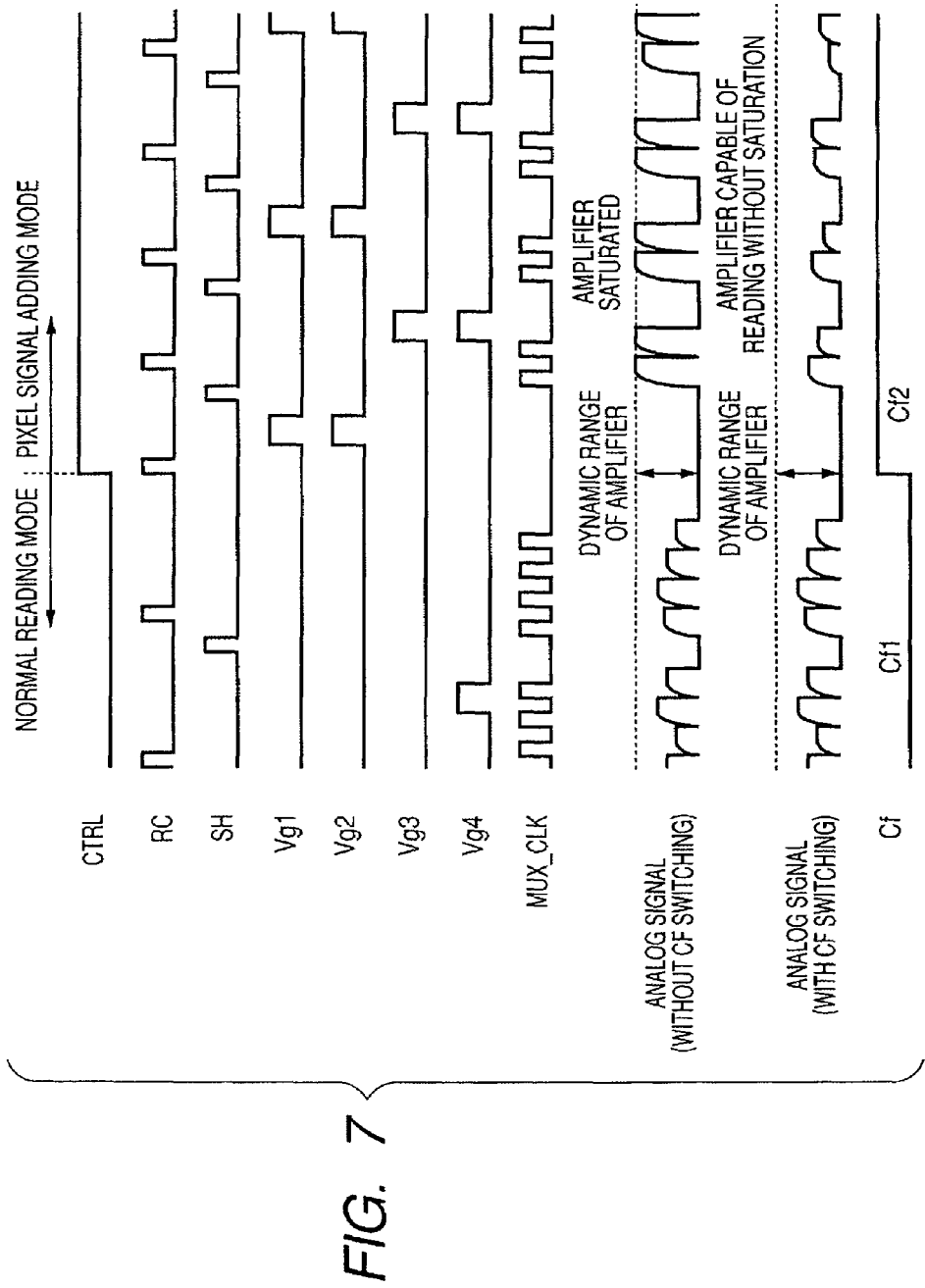
FIG. 7 is a timing chart showing the operation of the radiation image pickup apparatus according to the fourth embodiment of the invention.

FIG. 7 is a timing chart showing the operation of the radiation image pickup apparatus according to the fourth embodiment of the invention. FIG. 7 shows the case where the gate driving device 410 simultaneously drives the drive wirings Vg1 and Vg2 and simultaneously drives the drive wirings Vg3 and Vg4 by the control of the control unit 800. The analog signals which are outputted from the amplifiers A1 to A4 are shown in FIG. 7. In addition to the analog signals in the case where integration capacitors Cf of the amplifiers have been switched (the integration capacitor Cf1 in the "normal reading mode"; the integration capacitor Cf2 in the "pixel binning mode"), the analog signals in the case where integration capacitors Cf of the amplifiers are not switched irrespective of the mode (the integration capacitor Cf1 is fixedly used irrespective of the mode) are also shown in FIG. 7 for the purpose of comparison.

As shown in FIG. 7, in the case of the construction in which the integration capacitors Cf are not switched, the saturation of the amplifier occurs for the dynamic range of the amplifier in the "pixel binning mode". On the other hand, in the case of the construction in which the integration capacitors Cf are switched, it will be understood that the saturation of the amplifier for the dynamic range of the amplifier can be avoided even in the "pixel binning mode".

In the embodiment, in addition to the effect in the first embodiment, the saturation of the amplifier in the "pixel binning mode" can be prevented and the dynamic range characteristics of the radiation image pickup apparatus can be assured. Thus, the improvement of the noise resistance characteristics, the reading speed characteristics, and the dynamic range characteristics of the radiation image pickup apparatus can be realized. Although the fourth embodiment has the construction in which the two kinds of integration capacitors in the amplifiers are provided, many kinds of integration capacitors may be provided.

Fifth Embodiment

Figure 8:
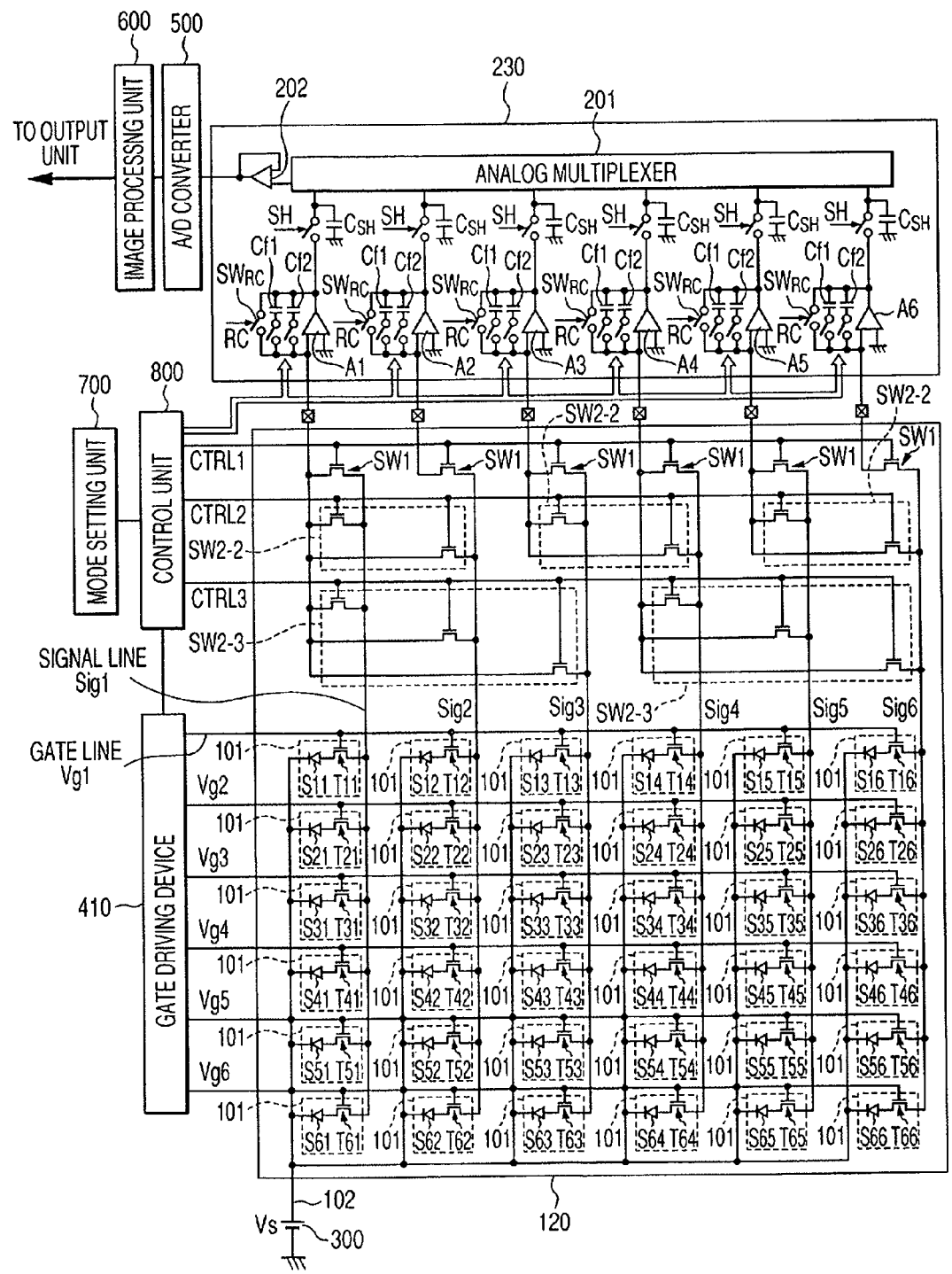
FIG. 8 is a schematic constructional diagram of a radiation image pickup apparatus according to the fifth embodiment of the invention.

FIG. 8 is a schematic constructional diagram of a radiation image pickup apparatus according to the fifth embodiment of the invention. In order to explain the radiation image pickup apparatus according to the fifth embodiment, 36 (6×6) pixels 101 in total are shown in a sensor array 120 shown in FIG. 8.

In the embodiment, in addition to in the "normal reading (1×1) mode", a "(2×2) pixel binning mode" and a "(3×3) pixel binning mode" are set as modes which are set by the mode setting unit 700. When those modes are set by the mode setting unit 700, in the case of the "normal reading (1×1) mode", the control unit 800 outputs the control signal CTRL1 shown in FIG. 8 and controls so as to drive the first switch SW1. In the case of the "(2×2) pixel binning mode", the control unit 800 outputs the control signal CTRL2 shown in FIG. 8 and controls so as to drive a second switch SW2-2 for adding the (2×2) pixel signals. Further, in the case of the "(3×3) pixel binning mode", the control unit 800 outputs a control signal CTRL3 shown in FIG. 8 and controls so as to drive a second switch SW2-3 for adding the (3×3) pixel signals.

Sixth Embodiment

Figure 9:
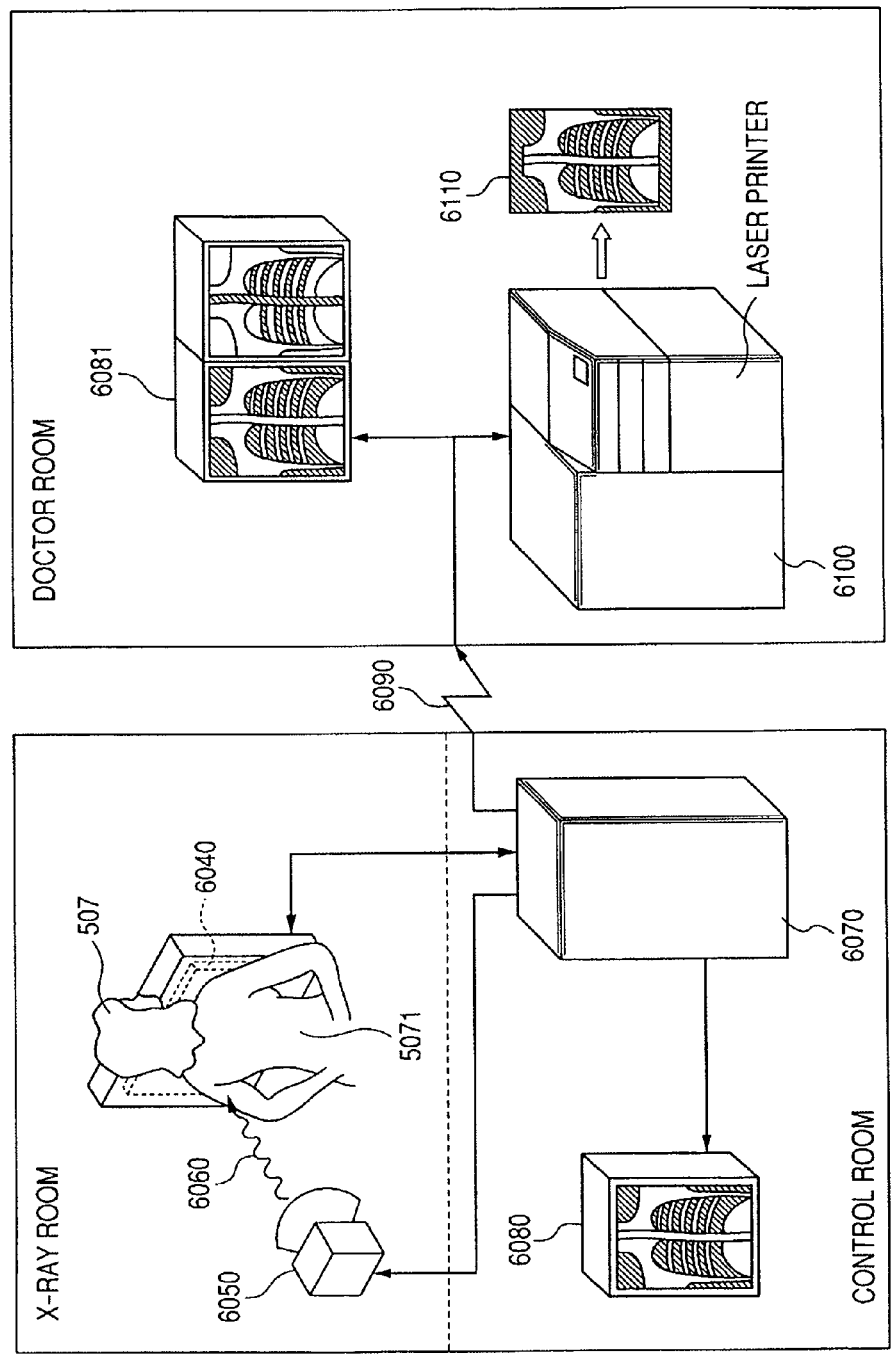
FIG. 9 shows the sixth embodiment of the invention and is a schematic diagram showing an example in which a radiation image pickup apparatus is applied to a radio-diagnostic system.

FIG. 9 shows the sixth embodiment of the invention and is a schematic diagram showing an example in which a radiation image pickup apparatus is applied to a radio-diagnostic (image pickup) system. An X-ray diagnostic system in which the X-ray is used as a radiation will now be described.

An X-ray 6060 generated by an X-ray tube 6050 as an X-ray generating unit is transmitted through a chest region 5071 of an object (patient) 507 and enters an image sensor 6040. Information showing the inside of a body of the object 507 is included in the X-ray which has entered the image sensor 6040. In the image sensor 6040, the incident X-ray is converted into visible light in a phosphor layer and the light is further photoelectrically converted, thereby obtaining signal charges (electric signal). The electric signal is converted into a digital signal, image-processed by an image processor 6070, displayed as an image onto a display 6080 in a control room, and observed.

The radiation image pickup apparatus according to each of the foregoing embodiments corresponds to, for example, the image sensor 6040. For instance, the mode setting unit 700, the control unit 800, the A/D converter 500, the image processing unit 600, and the like may be provided for the image processor 6070.

The image data formed by the image process by the image processor 6070 can be transferred to a remote place by transmitting means such as a telephone line 6090 or the like, can be displayed onto a display 6081 or stored into storing means such as an optical disk or the like at another place such as a doctor room or the like or a doctor at a remote place can diagnose such image data. The image data can be also recorded as a film 6110 by a film processor 6100.

Since the radiation image pickup apparatus according to each of the foregoing embodiments of the invention can accomplish both of the improvement of the noise resistance characteristics and the improvement of the reading speed, it is suitable for the X-ray image pickup system shown in FIG. 9.

The respective units shown in FIGS. 1, 5, 6, and 8 constructing the radiation image pickup apparatus according to each of the foregoing embodiments of the invention and the control method for the radiation image pickup apparatus can be realized by a method whereby a program stored in a RAM, a ROM, or the like of a computer operates. Such a program and a computer-readable storing medium in which the program has been stored are incorporated in the invention.

Specifically speaking, the program is recorded into the storing medium such as a CD-ROM and provided for the computer or it is provided thereto through various transmitting media. As a storing medium to record the program, besides the CD-ROM, a flexible disk, a hard disk, a magnetic tape, a magnetooptic disk, a non-volatile memory card, or the like can be used. As a transmitting medium of the program, it is possible to use a communicating medium (a wired line such as an optical fiber or the like, a wireless line, or the like) in a computer network (LAN, WAN such as Internet or the like, wireless communication network, or the like) system for propagating the program information as a carrier and supplying it.

The program is incorporated in the invention not only the case where the computer executes the supplied program, so that the functions of the radiation image pickup apparatus according to each of the foregoing embodiments of the invention are realized but also in the case where the program operates in cooperation with an OS (Operating System) which is operating in the computer, another application software, or the like and the functions of the radiation image pickup apparatus according to each of the foregoing embodiments of the invention are realized or the case where the all or a part of the processes of the supplied program are executed by a function expanding board or a function expanding unit of the computer and the functions of the radiation image pickup apparatus according to each of the foregoing embodiments of the invention are realized.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-236038, filed Aug. 16, 2005, which is hereby incorporated by reference herein in its entirety.

What is claimed is:

1. A radiation image pickup apparatus comprising:
 a sensor array constructed by two-dimensionally arranging a plurality of pixels each having a conversion element for converting radiation into an electric signal and a transfer switching element for transferring said electric signal from said conversion element;
 a plurality of signal wirings each adapted to connect a transfer switching element of said transfer switching elements of said plurality of pixels of said sensor array in a column direction;
 a reading circuit unit including a plurality of amplifiers provided in correspondence to said plurality of signal wirings, each of which amplifies an electric signal transferred from a transfer switching element of said transfer switching elements, and reads out an amplified signal;
 a switching unit adapted to switch electrical connections among said plurality of signal wirings and an electrical connection between a predetermined one of said plurality of signal wirings and an amplifier corresponding thereto, wherein said switching unit is arranged in front of said amplifier, and said switching unit switches between a first state where said plurality of signal wirings are electrically connected and said predetermined signal wiring and said amplifier corresponding thereto are electrically disconnected and a second state where said plurality of signal wirings are electrically disconnected and said predetermined signal wiring and said amplifier corresponding thereto are electrically connected;
 a mode setting unit adapted to set a mode in said radiation image pickup apparatus by switching between a normal reading mode in which an electric signal from one pixel is read out by a corresponding amplifier and a pixel binning mode in which electric signals from a set of pixels are added and an added signal is read out by one of said plurality of amplifiers corresponding to said set of pixels; and
 a control unit adapted to control said switching unit to switch between said first state and said second state in accordance with said mode set by said mode setting unit, and adapted to change a dynamic range of said amplifier, such that the dynamic range of said amplifier in the pixel binning mode is larger than the dynamic range of said amplifier in the normal reading mode.

2. The apparatus according to claim 1, wherein said switching unit is arranged between said plurality of signal wirings and said amplifier, and said switching unit includes:
 a first switch adapted to change an electrical connection and an electrical disconnection between said predetermined one of said plurality of signal wirings and an input stage of said amplifier corresponding thereto; and
 a second switch arranged among said plurality of signal wirings and at an input stage of said first switch, and adapted to change an electrical connection and an electrical disconnection among said plurality of signal wirings.

3. The apparatus according to claim 2,
 wherein said switching unit controls switching of said first switch and said second switch based on said mode set by said mode setting unit.

4. The apparatus according to claim 3,
wherein said control unit controls in such a manner that if said normal reading mode is set by said mode setting unit, said first switch is electrically connected and said second switch is electrically disconnected, and if said pixel binning mode is set by said mode setting unit, said first switch is electrically disconnected and said second switch is electrically connected.

5. The apparatus according to claim 4, further comprising:
a gate wiring including a plurality of gate lines each arranged along a row of said sensor array for controlling a continuity of said transfer switching elements; and
a gate drive circuit connected to said gate wiring, wherein, if said pixel binning mode is set by said mode setting unit, said control unit further controls said gate drive circuit to simultaneously drive some of said plurality of gate lines and scan.

6. The apparatus according to claim 4, further comprising a first capacitor element and a second capacitor element having different capacitance values, which are provided for each of said plurality of amplifiers and which accumulate an electric signal inputted to a corresponding amplifier, and
wherein said control unit controls in such a manner that if said normal reading mode is set by said mode setting unit, an electric signal is accumulated into a first capacitor element of said first capacitor elements, and if said pixel binning mode is set by said mode setting unit, an electric signal is accumulated into a second capacitor element of said second capacitor elements.

7. The apparatus according to claim 3, wherein said switching unit further includes a switch change-over unit adapted to change an electrical connection and an electrical disconnection of said first switch and said second switch, and said control unit controls a changing of said first switch and said second switch by controlling said switch change-over unit.

8. A radiation image pickup system comprising:
the radiation image pickup apparatus according to claim 1; and
a radiation generating unit adapted to emit a radiation.

9. A control method performed by a radiation image pickup apparatus, said method comprising:
a first step of setting a mode in a radiation image pickup apparatus that includes a sensor array constructed by two-dimensionally arranging a plurality of pixels each having a conversion element for converting radiation into an electric signal and a transfer switching element for transferring said electric signal from said conversion element, a plurality of signal wirings each adapted to connect a transfer switching element of said transfer switching elements of said plurality of pixels of said sensor array in a column direction, a reading circuit unit including a plurality of amplifiers provided in correspondence to said plurality of signal wirings, each of which amplifies an electric signal transferred from a corresponding transfer switching element and reads out an amplified signal, and a switching unit adapted to switch electrical connections among said plurality of signal wirings and an electrical connection between a predetermined one of said plurality of signal wirings and an amplifier corresponding thereto in front of said amplifier;
a second step of switching a state of said switching unit based on said mode set in said first step to either a first state where said plurality of signal wirings are electrically connected and said predetermined signal wiring and said amplifier corresponding thereto are electrically disconnected in front of said amplifier or a second state where said plurality of signal wirings are electrically disconnected and said predetermined signal wiring and said amplifier corresponding thereto are electrically connected in front of said amplifier;
a third step of setting a mode in said radiation image pickup apparatus by switching between a normal reading mode in which an electric signal from one pixel is read out by a corresponding amplifier and a pixel binning mode in which electric signals from a set of pixels are added and an added signal is read out by one of said plurality of amplifiers corresponding to said set of pixels; and
a fourth step of controlling said switching unit to switch between said first state and said second state in accordance with said mode set by said third step, and changing a dynamic range of said amplifier, such that the dynamic range of said amplifier is set larger in the pixel binning mode than the dynamic range of said amplifier in the normal reading mode.

10. A radiation image pickup apparatus comprising:
a sensor array constructed by two-dimensionally arranging a plurality of pixels each having a conversion element for converting radiation into an electric signal and a transfer switching element for transferring said electric signal from said conversion element;
a plurality of signal wirings each adapted to connect a transfer switching element of said transfer switching elements of said plurality pixels of said sensor array in a column direction;
a reading circuit unit including a plurality of amplifiers provided in correspondence to said plurality of signal wirings, each of which amplifies an electric signal transferred from a transfer switching element of said transfer switching elements, and reads out an amplified signal;
a switching unit adapted to switch electrical connections among said plurality of signal wirings and an electrical connection between a predetermined one of said plurality of signal wirings and an input stage of an amplifier corresponding thereto, wherein said switching unit is arranged in front of said amplifier, and said switching unit switches between a first state where said plurality of signal wirings are electrically connected and said predetermined signal wiring and said input stage of said amplifier corresponding thereto are electrically disconnected and a second state where said plurality of signal wirings are electrically disconnected and said predetermined signal wiring and said input stage of said amplifier corresponding thereto are electrically connected;
a mode setting unit adapted to set a mode in said radiation image pickup apparatus by switching between a normal reading mode in which an electric signal from one pixel is read out by a corresponding amplifier and a pixel binning mode in which electric signals from a set of pixels are added and an added signal is read out by one of said plurality of amplifiers corresponding to said set of pixels; and
a control unit adapted to control said switching unit to switch between said first state and said second state in accordance with said mode set by said mode setting unit, and adapted to change a dynamic range of said amplifier, such that the dynamic range of said amplifier in the pixel binning mode is larger than the dynamic range of said amplifier in the normal reading mode.

11. The apparatus according to claim 10, wherein said switching unit includes:
a first switch adapted to change an electrical connection and an electrical disconnection between said predetermined one of said plurality of signal wirings and said input stage of said amplifier corresponding thereto; and a second switch arranged among said plurality of signal wirings and at an input stage of said first switch, and adapted to change an electrical connection and an electrical disconnection among said plurality of signal wirings.

12. A radiation image pickup apparatus comprising:

a sensor array constructed by two-dimensionally arranging a plurality of pixels each having a conversion element for converting radiation into an electric signal and a transfer switching element for transferring said electric signal from said conversion element;

a plurality of signal wirings each adapted to connect a transfer switching element of said transfer switching elements of said plurality of pixels of said sensor array in a column direction;

a reading circuit unit including a plurality of amplifiers provided in correspondence to said plurality of signal wirings, each of which amplifies an electric signal transferred from a transfer switching element of said transfer switching elements, and reads out an amplified signal;

a switching unit adapted to switch electrical connections among said plurality of signal wirings and an electrical connection between a predetermined one of said plurality of signal wirings and an amplifier corresponding thereto, wherein said switching unit is arranged in front of said amplifier between said sensor array and said amplifier, and said switching unit switches between a first state where said plurality of signal wirings are electrically connected and said predetermined signal wiring and said amplifier corresponding thereto are electrically disconnected and a second state where said plurality of signal wirings are electrically disconnected and said predetermined signal wiring and said amplifier corresponding thereto are electrically connected, a mode setting unit adapted to set a mode in said radiation image pickup apparatus by switching between a normal reading mode in which an electric signal from one pixel is read out by a corresponding amplifier and a pixel binning mode in which electric signals from a set of pixels are added and an added signal is read out by one of said plurality of amplifiers corresponding to said set of pixels; and a control unit adapted to control said switching unit to switch between said first state and said second state in accordance with said mode set by said mode setting unit, and adapted to change a dynamic range of said amplifier, such that the dynamic range of said amplifier in the pixel binning mode is larger than the dynamic range of said amplifier in the normal reading mode.

13. The apparatus according to claim 12, wherein said switching unit includes:

a first switch adapted to change an electrical connection and an electrical disconnection between said predetermined one of said plurality of signal wirings and an input stage of said amplifier corresponding thereto; and a second switch arranged among said plurality of signal wirings and at an input stage of said first switch, and adapted to change an electrical connection and an electrical disconnection among said plurality of signal wirings.

* * * * *